US010598803B2

(12) United States Patent
Deng

(10) Patent No.: US 10,598,803 B2
(45) Date of Patent: Mar. 24, 2020

(54) SYSTEMS AND METHODS FOR ASSESSING TIME OF FLIGHT PERFORMANCE OF POSITRON EMISSION TOMOGRAPHY SCANNER

(71) Applicant: SHANGHAI UNITED IMAGING HEALTHCARE CO., LTD., Shanghai (CN)

(72) Inventor: Zilin Deng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/377,350

(22) Filed: Apr. 8, 2019

(65) Prior Publication Data

US 2019/0235098 A1    Aug. 1, 2019

Related U.S. Application Data

(63) Continuation of application No. 16/020,998, filed on Jun. 27, 2018, now Pat. No. 10,254,420, which is a
(Continued)

(30) Foreign Application Priority Data

Sep. 30, 2016    (CN) .......................... 2016 1 0877357

(51) Int. Cl.
*G01T 1/202* (2006.01)
*G01T 1/29* (2006.01)
(Continued)

(52) U.S. Cl.
CPC ............ *G01T 1/2985* (2013.01); *A61B 6/037* (2013.01); *G01T 1/202* (2013.01); *G01T 1/2018* (2013.01); *G01T 7/00* (2013.01)

(58) Field of Classification Search
CPC ..... A61B 6/037; G01T 1/2985; G01T 1/2018; G01T 1/202; G01T 7/00
See application file for complete search history.

(56) References Cited

U.S. PATENT DOCUMENTS 7,417,231 B2    8/2008    Defrise et al.
8,796,637 B1    8/2014    Burr et al.
(Continued)

FOREIGN PATENT DOCUMENTS

WO    2010085150 A1    7/2010
WO    2018059459 A1    4/2018

OTHER PUBLICATIONS

Feing Wang et al., Study of Time-of-light Influence on Image Quality by PET/CT Scanner, Chinese Medical Equipment Journal, 34(1): 8-11, 2013.
(Continued)

*Primary Examiner* — David P Porta
*Assistant Examiner* — Fani Boosalis
(74) *Attorney, Agent, or Firm* — Metis IP LLC

(57) ABSTRACT

A method for assessing the time of flight (TOF) performance of a positron emission tomography (PET) scanner is provided. The method may include obtaining raw data relating to radiation originating from an object from a PET scan by a PET scanner, the raw data including TOF information. The method may also include generating, based on a back projection algorithm, a first back projection image by reconstructing the raw data including the TOF information. The method may further include generating, based on the back projection algorithm, a second back projection image by reconstructing the raw data excluding the TOF information. The method may further include comparing the first back projection image with the second back projection image.
(Continued)

The method may also include assessing, based on the comparison, the TOF performance of the PET scanner.

20 Claims, 11 Drawing Sheets

Related U.S. Application Data continuation of application No. PCT/CN2017/103779, filed on Sep. 27, 2017.

(51) Int. Cl.
*A61B 6/03* (2006.01)
*G01T 1/20* (2006.01)
*G01T 7/00* (2006.01)

(56) References Cited

U.S. PATENT DOCUMENTS

| | | |
|---|---|---|
| 9,111,381 B2 | 8/2015 | Levin et al. |
| 2006/0097175 A1 | 5/2006 | Ganin et al. |
| 2006/0163485 A1 | 7/2006 | Stearns et al. |
| 2008/0284428 A1 | 11/2008 | Fiedler et al. |
| 2010/0074500 A1 | 3/2010 | Defrise et al. |
| 2012/0070057 A1 | 3/2012 | Zhang et al. |
| 2014/0003689 A1 | 1/2014 | Asma et al. |

OTHER PUBLICATIONS

Tianqi Wu et al., Research on Impact of Time of Flight Acquisition and High Definition Reconstruction on PET/CT Image Quality, China Medical Equipment, 12(1): 2-5, 2016.

Feng Wang et al., Research on Performances of PET/CT with Time-of-flight Capability, China Medical Equipment, 9(7): 1-5, 2012.

International Search Report in PCT/CN2017/103779 dated Jan. 17, 2018, 5 pages.

Written Opinion of the International Searching Authority in PCT/CN2017/103779 dated Jan. 17, 2018, 5 pages.

First Office Action for Chinese application No. 201610877357.7 dated May 31, 2018, 12 pages.

Qiyong Guo et al., Chinese Clinical Medical Imaging PET and Molecular , 242-243, 2015.

SYSTEMS AND METHODS FOR ASSESSING TIME OF FLIGHT PERFORMANCE OF POSITRON EMISSION TOMOGRAPHY SCANNER

CROSS-REFERENCE TO RELATED APPLICATIONS

This application is a continuation of U.S. application Ser. No. 16/020,998, filed on Jun. 27, 2018, which is a continuation of International Application No. PCT/CN2017/103779, filed on Sep. 27, 2017, which claims priority to Chinese Patent Application No. 201610877357.7, filed on Sep. 30, 2016, the entire contents of which are hereby incorporated by reference.

TECHNICAL FIELD

The present disclosure generally relates to systems and methods for assessing the performance of medical machines, and more specifically relates to systems and methods for assessing the TOF performance of a positron emission tomography (PET) scanner.

BACKGROUND

The TOF-PET technique is more widely used in clinical diagnosis to improve image quality. However, the TOF performance of a TOF-PET scanner may decline after usage of the TOF-PET scanner for a period of time. The TOF performance of the TOF-PET scanner may be assessed periodically or from time to time. According to existing techniques for assessing the TOF performance of a PET scanner, one or more images may be reconstructed and one or more correction operations such as a normalized correction, an attenuation correction, or a system dead time correction may be performed in the reconstruction process. Such techniques may be time-consuming and costly. Therefore, it is desirable to provide systems and methods for assessing the TOF performance of a PET scanner with improved efficiency.

SUMMARY

In a first aspect of the present disclosure, a system for assessing a TOF performance of a PET scanner may include at least one storage device and at least one processor configured to communicate with the at least one storage device. The at least one storage device may include a set of instructions. When the at least one processor executing the set of instructions, the at least one processor may be directed to perform one or more of the following operations. The at least one processor may obtain raw data relating to radiation originating from an object from a positron emission tomography (PET) scan by a PET scanner. The at least one processor may generate, based on a back projection algorithm, a first back projection image by reconstructing the raw data including time of flight (TOF) information. The at least one processor may generate, based on the back projection algorithm, a second back projection image by reconstructing the raw data without the TOF information. The at least one processor may compare the first back projection image with the second back projection image. The at least one processor may assess, based on the comparison, A TOF performance of the PET scanner.

In some embodiments, a distribution of the radiation originating from the object may be symmetric with respect to a geometrical center of the object.

In some embodiments, the distribution of the radiation in the object may have a shape of a bucket, a rod, or a column.

In some embodiments, the at least one processor may perform at least one of a normalized correction, an attenuation correction, or a system dead time correction to the raw data.

In some embodiments, to compare the first back projection image with the second back projection image, the at least one processor may determine one or more two-dimensional (2D) ratio images based on the first back projection image and the second back projection image. For each of the one or more 2D ratio images, the at least one processor may determine one or more degrees of symmetry of pixel values of a plurality of pixels in the 2D ratio image.

In some embodiments, to determine one of the one or more 2D ratio images, the at least one processor may determine a plurality of voxel ratios based on voxel values of voxels in the first back projection image and voxel values of corresponding voxels in the second back projection image. The at least one processor may generate a three-dimensional (3D) ratio image including a plurality of voxels corresponding to the plurality of voxel ratios. The at least one processor may determine the 2D ration image by selecting a 2D section of the 3D ratio image. The 2D section of the 3D ratio image may include a plurality of pixels. A pixel value of a pixel in the 2D section may be equal to the voxel ratio of a corresponding voxel in the 3D ratio image.

In some embodiments, to determine one of the one or more 2D ratio images, the at least one processor may select a first 2D section of the first back projection image. The first section may include a plurality of first pixels. A pixel value of a first pixel may be equal to a voxel value of a corresponding voxel in the first back projection image. The at least one processor may select a second 2D section of the second back projection image. The second section may include a plurality of second pixels. The plurality of second pixels may correspond to the plurality of first pixels. A pixel value of a second pixel may be equal to a voxel value of a corresponding voxel in the second back projection image. The at least one processor may determine a plurality of pixel ratios based on the pixel values of the plurality of first pixels and the pixel values of the plurality of second pixels. The at least one processor may generate the 2D ratio image including a plurality of third pixels corresponding to the plurality of pixel ratios.

In some embodiments, to determine each of the one or more degrees of symmetry of the pixel values of the plurality of pixels in each of the one or more 2D ratio images, the at least one processor may determine a center of symmetry or an axis of symmetry in the 2D ratio image. The at least one processor may determine one or more pixel pairs each of which includes two pixels in the 2D ratio image. The two pixels may be symmetric about the center of symmetry or the axis of symmetry. For each of the one or more pixel pairs, the at least one processor may determine an absolute value of a difference between pixel values of the two pixels in the pixel pair. The at least one processor may determine an average value of the absolute values of the differences associated with the one or more pixel pairs. The average value may represent the degree of symmetry.

In some embodiments, to assess, based on the comparison, the TOF performance of the PET scanner, the at least one processor may assess the TOF performance of the PET scanner based on the one or more degrees of symmetry.

According to another aspect of the present disclosure, a method for assessing a TOF performance of a PET scanner may include one or more of the following operations. At least one processor may obtain raw data relating to radiation originating from an object from a positron emission tomography (PET) scan by a PET scanner. The at least one processor may generate, based on a back projection algorithm, a first back projection image by reconstructing the raw data including time of flight (TOF) information. The at least one processor may generate, based on the back projection algorithm, a second back projection image by reconstructing the raw data without the TOF information. The at least one processor may compare the first back projection image with the second back projection image. The at least one processor may assess, based on the comparison, a TOF performance of the PET scanner.

In some embodiments, the object may be located at a center region of a field of view (FOV) of the PET scanner.

In some embodiments, the generating of the first back projection image by reconstructing the raw data including the TOF information based on the back projection algorithm may comprises generating the first back projection image based on one or more first projection angles of a first range from 0° to 360°. The generating of the second back projection image by reconstructing the raw data excluding the TOF information based on the back projection algorithm comprises generating the second back projection image based on one or more second projection angles of a second range from 0° to 360°.

According to yet another aspect of the present disclosure, a non-transitory computer readable medium may comprise at least one set of instructions. The at least one set of instructions may be executed by at least one processor of a computing device. The at least one processor may obtain raw data relating to radiation originating from an object from a positron emission tomography (PET) scan by a PET scanner. The at least one processor may determine imaging data based on the raw data. The at least one processor may generate, based on a back projection algorithm, a first back projection image by reconstructing the imaging data including time of flight (TOF) information. The at least one processor may generate, based on the back projection algorithm, a second back projection image by reconstructing the imaging data without the TOF information. The at least one processor may compare the first back projection image with the second back projection image. The at least one processor may assess, based on the comparison, a TOF performance of the PET scanner.

According to yet another aspect of the present disclosure, a system for assessing a TOF performance of a PET scanner may comprise: an raw data obtaining module configured to obtain raw data relating to radiation originating from an object from a positron emission tomography (PET) scan by a PET scanner; a first back projection module configured to generate, based on a back projection algorithm, a first back projection image by reconstructing the raw data including time of flight (TOF) information; a second back projection module configured to generate, based on the back projection algorithm, a second back projection image by reconstructing the raw data without the TOF information; a comparison module configured to compare the first back projection image with the second back projection image; and a TOF performance assessment module configured to assess, based on the comparison, a TOF performance of the PET scanner.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
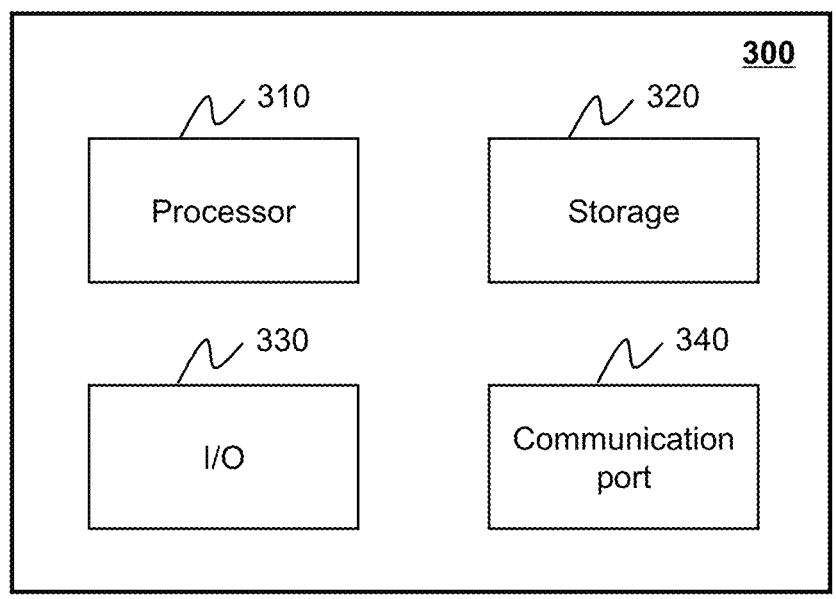
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for assessing the TOF performance of a PET scanner. In the present disclosure, a processing device may generate a first three-dimensional (3D) image using a back projection algorithm based on TOF information, and a second 3D image using the back projection algorithm without the TOF information. The processing device may generate a two-dimensional (2D) ratio image. The pixel values of the 2D image may be ratios between a part of voxel values of the first 3D image and a part of voxel values of the second 3D image. The processing device may determine a degree of symmetry of the pixel values in the 2D ratio image. A higher the degree of symmetry may indicate a better TOF performance of the PET scanner.

According to the present disclosure, the 3D image may be generated without an correction operation, such as a normalized correction, an attenuation correction, and a system dead time correction, which may reduce the complexity and improve the efficiency of the assessment of the TOF performance of a PET scanner.

The following description is provided to help better understanding systems and/or methods for assessing the TOF performance of a PET scanner. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
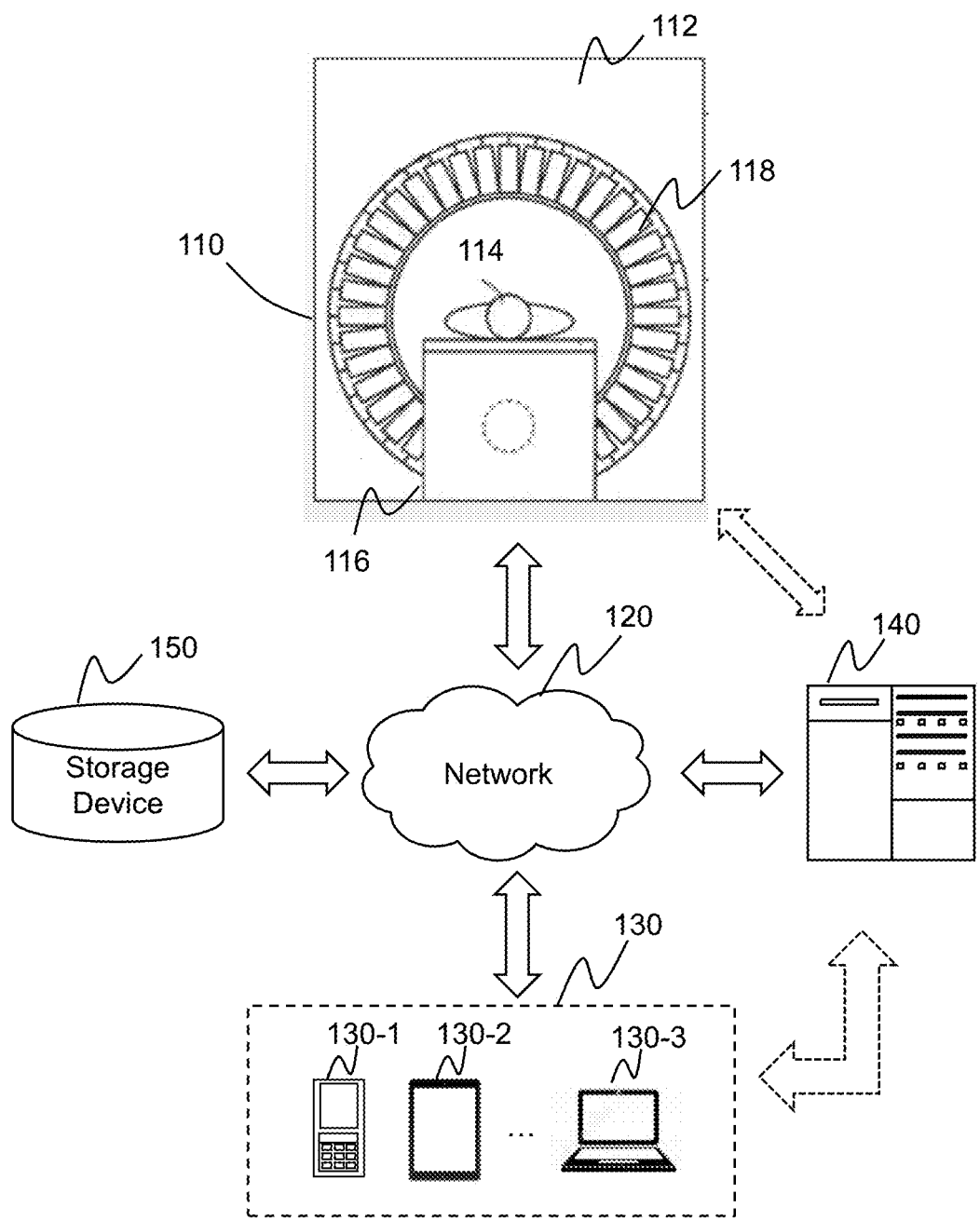
FIG. 1 is a schematic diagram illustrating an exemplary positron emission tomography (PET) system according to some embodiments of the present disclosure.

FIG. 1 is a schematic diagram illustrating an exemplary positron emission tomography (PET) system according to some embodiments of the present disclosure. PET imaging is based on coincidence events corresponding to detected photons arising from positron-electron annihilation. The time required for a photon to travel from its origin to a point where it is detects is referred to as the time of flight (TOF) of the photon. Time of flight (TOF) positron emission tomography (PET) ("TOF-PET") is based on measurement of a time difference between the TOFs of two gamma photons arising from a positron-electron annihilation. The TOF measurement may be used to determine the location at which a positron-electron annihilation has taken place.

The PET system 100 may include a PET scanner 110, a network 120, a terminal 130, a processing device 140, and a storage device 150. The components in the PET system 100 may be connected in one or more of various manners. Merely by way of example, the PET scanner 110 may be connected to the processing device 140 through the network 120. As another example, the PET scanner 110 may be connected to the processing device 140 directly (shown as the bi-directional arrow in dotted line linking the PET scanner 110 and the processing device 140). As another example, the processing device 140 may be connected to the storage device 150 through the network 120 or directly. As a further example, the processing device 140 may be connected to a terminal device (e.g., 130-1, 130-2, 130-3, etc.) through the network 120. As still a further example, the processing device 140 may be connected to a terminal device (e.g., 130-1, 130-2, 130-3, etc.) directly (shown as the bi-directional arrow in dotted line linking the terminal 130 and the processing device 140).

The PET scanner 110 may include a gantry 112, a table 116, and a detector 118. An object 114 injected with a tracer (e.g., radiopharmaceutical) may be placed on the table 116. The gantry 112 may support the detector 118. The gantry 112 may form a detection tunnel (not shown in FIG. 1).

The tracer refers to a radioactive substance that may decay and emit positrons. The radiopharmaceutical refers to a drug having radioactivity, which is introduced into the object 114 for the purposes of diagnosis and treatment. The object 114 may be biological or non-biological. Merely by way of example, the object 114 may include a patient, a man-made object, etc. As another example, the object 114 may include a specific portion, organ, and/or tissue of the patient. For example, the object 114 may include the head, the brain, the neck, the body, a shoulder, an arm, the thorax, the heart, the stomach, a blood vessel, a soft tissue, a knee, a foot, or the like, of a patient, or any combination thereof.

Figure 2:
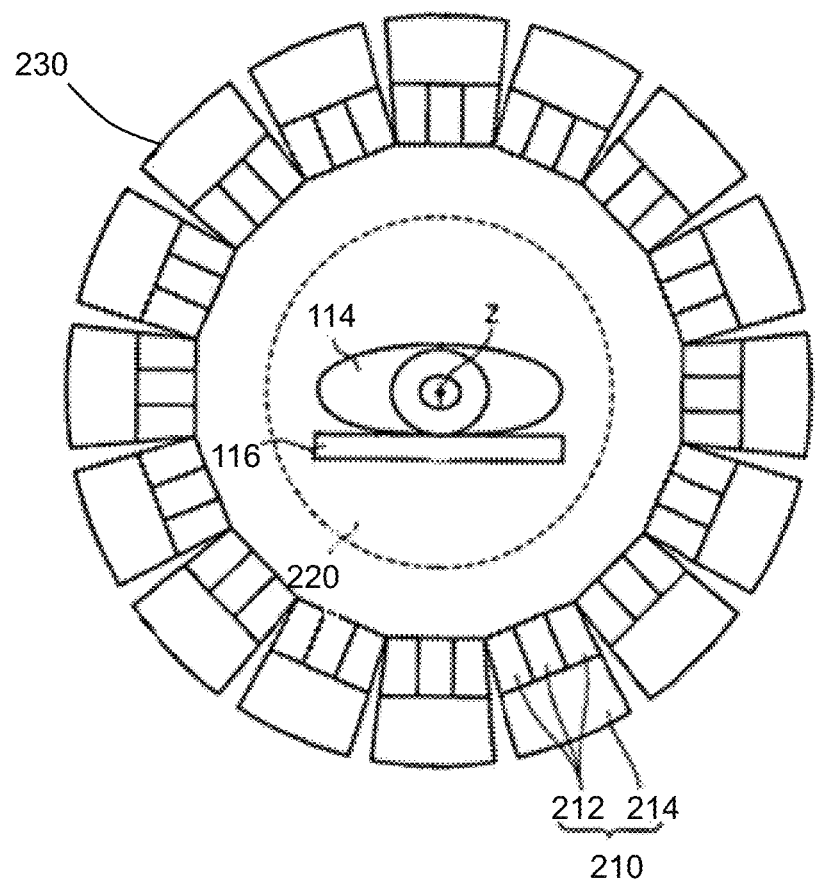
FIG. 2 is a cross section of an exemplary PET scanner according to some embodiments of the present disclosure.

As shown in FIG. 2, the detector 118 may include a plurality of detector rings (e.g., a detector ring 230) arranged along the Z direction (perpendicular to the paper as shown in FIG. 2). The plurality of detector rings may be located around the detection tunnel. A detector ring may include a plurality of detector units (e.g., a detector unit 220) arranged along the circumference of the detector ring.

The detector 118 may form a cavity to accommodate the table 116. There may be a field of view (FOV) 220 in the cavity. During a scan process, the object 114 along with the table 116 may be moved into the cavity to position a region of interest (ROI) of the object 114 in the FOV 220 and make the central axis of the object 114 substantially overlap with the central axis Z of the FOV 220, to facilitate the symmetry of data (e.g., electrical signals) generated by the detector 118. In some embodiments, the deviation between the center axis of the object 114 and the center axis Z of the FOV 220 may be within 5 millimeters (mm).

As shown in FIG. 2, a detector unit 210 may include a scintillator 212 and a photodetector 214. In some embodiments, the photodetector 214 may be a photomultiplier (PMT). The photodetector 214 may be coupled to the scintillator 212. In some embodiments, the scintillator 212 may include an array of scintillation crystals.

In some embodiments, positrons emitted from the radiation may travel through the object 114 until they encounter electrons. When a positron and an electron meet, annihilation may occur. The electron-positron annihilation may simultaneously generate two 511-kiloelectron volt (keV) gamma photons traveling in opposite directions along a line. The two gamma photons may be detected by a pair of oppositely disposed detector units. This example and the following descriptions in which two gamma photons are generated in an annihilation event is provided for illustration purposes and not intended to limit the scope of the present disclosure. It is understood that the systems and methods disclosed herein may be applied in the assessment of the TOF performance of a PET scanner in which photons of other types or energy levels are generated and detected for image reconstruction.

A gamma photon generated by an electron-positron annihilation may strike the scintillator 212 to produce bursts of visible or invisible light. The visible or invisible light may transmit from the scintillator 212 to the photodetector 214. The visible or invisible light may be converted to an electrical signal (e.g., an electrical pulse) by the photodetector 214. The electrical signal may be transmitted to other components of the PET system 100, such as the processing device 140.

In some embodiments, the detector unit 210 may further include a light guide (not shown in FIG. 2) configured to provide a light path to the photodetector 214. In some embodiments, a front-end circuit board (not shown in FIG. 2) may be coupled to the photodetector 214 to process electrical signals and/or transmit electrical signals to other components (e.g., the processing device 140) of the PET system 100.

The network 120 may facilitate exchange of information and/or data. In some embodiments, one or more components in the PET system 100 (e.g., the PET scanner 110, the terminal 130, the processing device 140, or the storage device 150) may send information and/or data to other component(s) in the PET system 100 via the network 120. For example, the processing device 140 may obtain electrical signals from the PET scanner 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. The terminal 130 may remotely operate the PET scanner 110. In some embodiments, the terminal 130 may operate the PET scanner 110 via a wireless connection. In some embodiments, the terminal 130 may receive information and/or instructions inputted by a user, and transmit the received information and/or instructions to the PET scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the PET scanner 110, the terminal 130, or the storage device 150. For example, the processing device 140 may process electrical signals obtained from the PET scanner 110 and reconstruct an image based on the obtained electrical signals. In some embodiments, the processing device 140 may be a single server, or a server group. The server group may be centralized, or distributed. In some embodiments, the processing device 140 may be local or remote. For example, the processing device 140 may access information and/or data stored in the PET scanner 110, the terminal 130, and/or the storage device 150 via the network 120. As another example, the processing device 140 may be directly connected to the PET scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the terminal 130 and/or the processing device 140. For example, the storage device 150 may store images generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to assess the TOF performance of the PET scanner 110. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the PET system 100 (e.g., the processing device 140, the terminal 130). One or more components of the PET system 100 may access the data or instructions stored in the storage device 150 via the network 120. In some embodiments, the storage device 150 may be directly connected to or communicate with one or more components in the PET system 100 (e.g., the processing device 140, the terminal 130). In some embodiments, the storage device 150 may be part of the processing device 140.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may process data obtained from the PET scanner 110, the terminal 130, the storage device 150, or any other component of the PET system 100. Specifically, the processor 310 may process electrical signals obtained from the PET scanner 110. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be note that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both step A and step B, it should be understood that step A and step B may also be performed by two different processors jointly or separately in the computing device 300 (e.g., a first processor executes step A and a second processor executes step B, or the first and second processors jointly execute steps A and B).

The storage 320 may store data/information obtained from the PET scanner 110, the terminal 130, the storage device 150, or any other component of the PET system 100.

In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for assessing the TOF performance of the PET scanner 110.

The I/O 330 may input or output signals, data, or information. In some embodiments, the I/O 330 may enable a user interaction with the processing device 140. For example, the processing device may display an image through the I/O 330. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the PET scanner 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
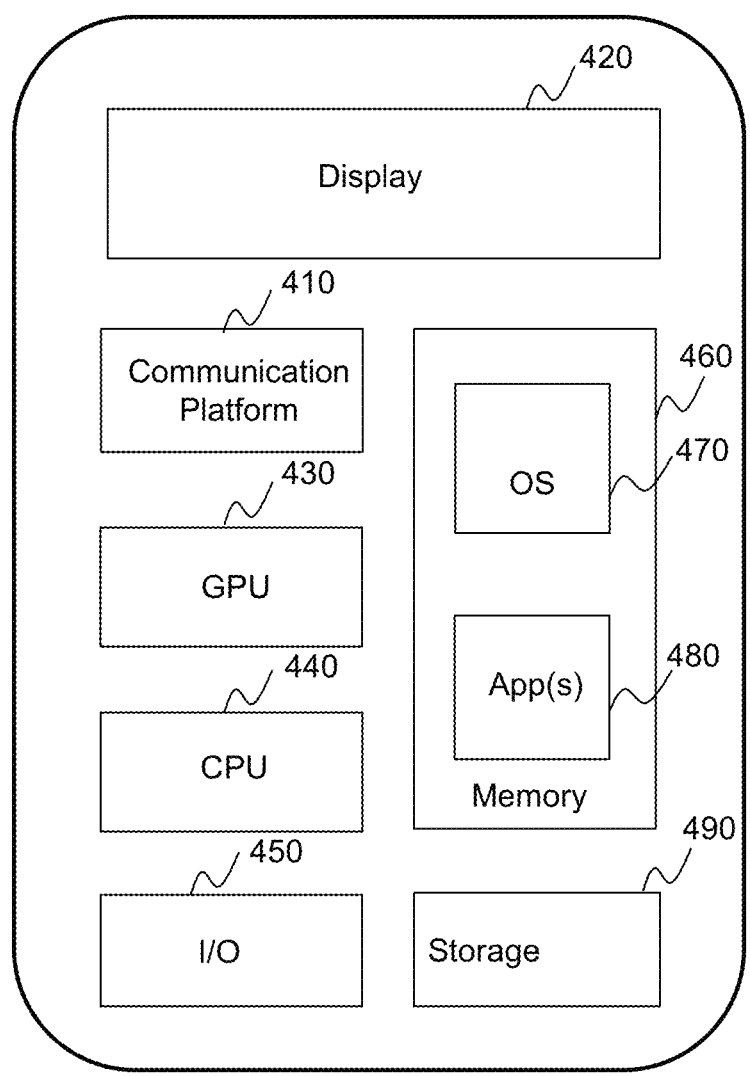
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
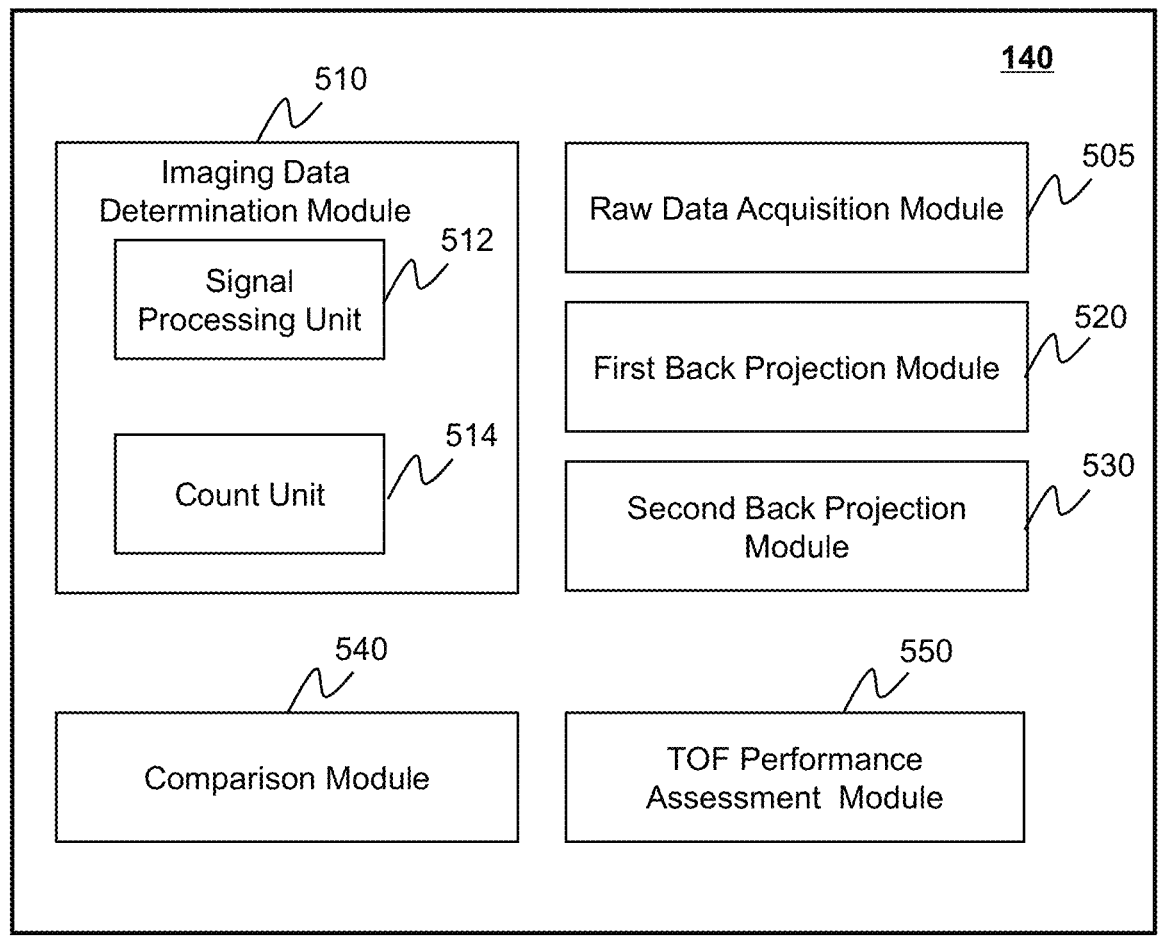
FIG. 5 is a block diagram illustrating an exemplary processing device according to some embodiments of the present disclosure.

FIG. 5 is a block diagram illustrating an exemplary processing device according to some embodiments of the present disclosure. The processing device 140 may include a raw data acquisition module 505, an imaging data determination module 510, a first back projection module 520, a second back projection module 530, a comparison module 540, and a TOF performance assessment module 550.

The raw data acquisition module 505 may obtain raw data (also referred to as list-mode raw data or sinogram mode raw data) relating to radiation originating from an object detected in a PET scan by a PET scanner. The raw data may include the electrical signals generated by the detector 118 of the PET scanner 110 as described elsewhere in the present disclosure. See, e.g., FIG. 1 and the description thereof. The radiation may originate from a radioactive substance (e.g., radiopharmaceutical) (also referred to as a radiation source) that may decay and emit positrons. The radiopharmaceutical refers to a drug having radioactivity, which is introduced into the object for the purposes of diagnosis and treatment. The object may be biological or non-biological. Merely by way of example, the object may include a patient, a man-made object, etc. As another example, the object may include a specific portion, organ, and/or tissue of the patient. For example, the object may include the head, the brain, the neck, the body, a shoulder, an arm, the thorax, the heart, the stomach, a blood vessel, a soft tissue, a knee, a foot, or the like, of a patient, or any combination thereof.

In some embodiments, the object may include a phantom with a shape of a bucket, a rod, a column, or the like, or any combination thereof. For example, for a phantom with a bucket shape, the phantom may be a solid bucket, or a bucket containing a filler material such as a liquid. In some embodiments, the distribution of the radiation originating from the object may be symmetric. For example, the distribution of the radiation originating from the object may be symmetric with respect to a geometric center of the object. In some embodiments, the radiation in the object may distribute within the shape of the object. For example, for an object (e.g., a phantom) with a column shape, the distribution of the radiation originating from the object (e.g., the phantom) may be symmetric with respect to a geometric center of the object, and the radiation in the object (e.g., the phantom) may distribute within the shape of a column.

The imaging data determination module 510 may determine imaging data based on the raw data (e.g., the electrical signals generated by the detector 118). The imaging data may be used to generate one or more images. The imaging data determination module 510 may include a signal processing unit 512 and a count unit 514.

The signal processing unit 512 may determine single event data based on the electrical signals obtained from the PET scan by the PET scanner 110. A single event refers to the generation of a gamma photon. The single event data of a single event may include a detection time at which the detector 118 detects a gamma photon, a detection location at which the detector 118 detects the gamma photon, the energy of the gamma photon, or the like, or any combination thereof.

An electrical signal may have an amplitude that indicates the strength of the electrical signal. An amplitude may correspond to a time point. In some embodiments, the signal processing unit 512 may monitor the amplitudes of the electrical signals obtained from the PET scan by the PET scanner 110. When the signal processing unit 512 detects that an amplitude is greater than a predetermined threshold, the signal processing unit 512 may record the time point corresponding to the amplitude as the detection time of a gamma photon. In some embodiments, the detection location of a gamma photon refers to a position on the scintillator 212 where the gamma photon strikes. The signal processing unit 512 may determine the energy of a gamma photon based on the amplitude corresponding to the detection time of the gamma photon.

The count unit 514 may determine a plurality of coincidence events and coincidence event data of the plurality of coincidence events based on the single event data. A coincidence event may include two single events of which the two gamma photons arise from a same positron-electron annihilation. A coincidence event may correspond to a positron-electron annihilation.

The count unit 514 may preset a time window (e.g., the range from 6 ns to 18 ns). If a time difference between two detection times of two gamma photons is within the time window, the count unit 514 may designate the two single events corresponding to the two gamma photons as a coincidence event. In some embodiments, a positron-electron annihilation may be assumed to take place at a point on a line linking two detector units that detect the two gamma photons generated in the positron-electron annihilation. The line is referred to as a "line of response" (LOR). A coincidence event and/or a positron-electron annihilation may correspond to an LOR. The coincidence event data of a coincidence event may include an LOR corresponding to the coincidence event, the total number of detected coincidence events corresponding to the LOR, or the like, or any combination thereof.

The count unit 514 may further determine TOF information of the plurality of coincidence events. The TOF information of a coincidence event may include a time difference (e.g., a TOF difference) between two detection times of two gamma photons in the coincidence event, an estimated annihilation location on an LOR where the two gamma photons are generated in the coincidence event (or an estimated annihilation location on an LOR at which a positron-electron annihilation corresponding to the coincidence event takes place), or the like, or any combination thereof. The count unit 514 may determine the estimated annihilation location based on the TOF difference and the speed of the gamma photons travel within the object (e.g., speed of light). The estimated annihilation location of a coincidence event may indicate a probability distribution of annihilation location on the LOR at which two gamma photons are generated in the coincidence event.

In some embodiments, the imaging data may include the coincidence event data. The imaging data may further include the TOF information.

The first back projection module 520 may generate, based on a back projection algorithm, a first back projection image by reconstructing the imaging data including time of flight (TOF) information. The first back projection image may be a two-dimensional (2D) image or a three-dimensional (3D) image. For a coincidence event, an estimated annihilation location (e.g., a probability distribution of the annihilation location) on an LOR may be determined based on the TOF information of the coincidence event (e.g., the time difference). Similarly, one or more estimated annihilation locations (e.g., one or more probability distribution of the annihilation location(s)) on the LOR corresponding to one or more coincidence events may be determined based on the TOF information of the coincidence event(s). The first back projection module 520 may determine the first back projection image by reconstructing the imaging data including the estimated annihilation location(s) (e.g., the probability distribution(s) of the annihilation location(s)) on the LOR corresponding to the coincidence event(s) using the back projection algorithm. In some embodiments, the generated first back projection image may include a plurality of voxels or pixels.

The second back projection module 530 may generate, based on aback projection algorithm, a second back projection image by reconstructing the imaging data excluding the TOF information. In some embodiments, the back projection algorithm used by the second back projection module 530 may be the same as the back projection algorithm used by the first back projection module 520. The second back projection image may be a 2D image or a 3D image. For a coincidence event, the probabilities of the annihilation location on an LOR may be set same on the LOR if the TOF information is not considered. That is, the probability distribution of the annihilation location on the LOR may be same. The second back projection module 530 may determine the second back projection image by reconstructing the imaging data with same probability distributions on the LOR using the back projection algorithm. In some embodiments, the generated second back projection image may include a plurality of voxels or pixels.

The comparison module 540 may compare the first back projection image with the second back projection image. In some embodiments, because the first back projection image is generated based on the TOF information, and the second back projection image is generated without the TOF information, ratios of the voxel values (or the pixel values) of the first back projection image to the voxel values (or the pixel values) of the second back projection image may reflect the TOF performance of the PET scanner 110. In some embodiments, because the radiation distributes symmetrically in the object (e.g., a phantom), the better the TOF performance of the PET scanner 110 is, the higher the degree of symmetry of the ratios may be. Therefore, the comparison module 540 may determine a degree of symmetry of the ratios to assess the TOF performance of the PET scanner 110.

The TOF performance assessment module 550 may assess, based on the comparison, the TOF performance of the PET scanner. In some embodiments, the TOF performance assessment module 550 may assess the TOF performance based on the degree of symmetry.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units. For example, the first back projection module 520 may be integrated into the second back projection module as a single module that may both determine the first back projection image and the second back projection image. As another example, the comparison module 540 may be divided into two units. The first unit may be configured to determine a 2D ratio image. The second unit may be configured to determine a degree of symmetry based on the 2D ratio image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of components of the processing device 140 may include a storage apparatus. Additionally or alternatively, the components of the computing device 120 may share a common storage apparatus.

Figure 6:
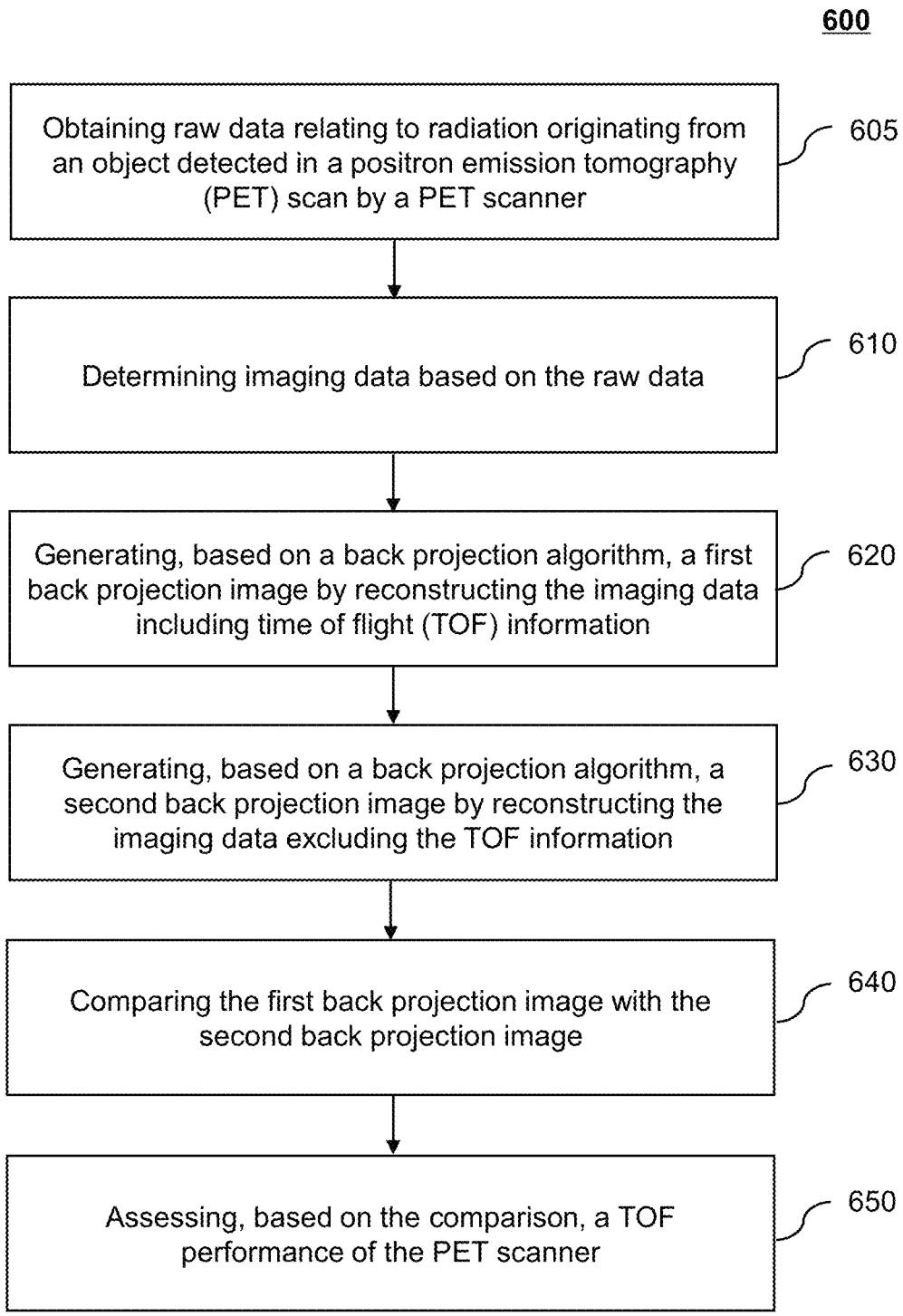
FIG. 6 is a flowchart illustrating an exemplary process for assessing TOF performance of a PET scanner according to some embodiments of the present disclosure.

FIG. 6 is a flowchart illustrating an exemplary process for assessing TOF performance of a PET scanner according to some embodiments of the present disclosure. The process 600 may be implemented in the PET system 100 illustrated in FIG. 1. For example, the process 600 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 605, the raw data acquisition module 505 may obtain raw data (also referred to as list-mode raw data or sinogram mode raw data) relating to radiation originating from an object detected in a positron emission tomography (PET) scan by a PET scanner. In some embodiments, the raw data may include the electrical signals generated by the detector 118 of the PET scanner 110 as described elsewhere in the present disclosure. See, e.g., FIG. 1, and the description thereof. As illustrated herein, the object may be a phantom with a shape of a bucket, a rod, a column, or the like, or any combination thereof. For example, for a phantom with a bucket shape, the phantom may be a solid bucket, or a bucket containing a filler material such as a liquid. In some embodiments, the distribution of the radiation originating from the object may be symmetric, specifically, symmetric with respect to a geometric center of the object. For example, for an object (phantom) with a column shape, the distribution of the radiation originating from the object may be symmetric with respect to a geometric center of the object.

In 610, the imaging data determination module 510 may determine imaging data based on the raw data (e.g., the electrical signals generated by the detector 118). The imaging data may be used to generate one or more images. In some embodiments, the imaging data may include coincidence event data of a plurality of coincidence events. The coincidence event data of a coincidence event may include an LOR corresponding to the coincidence event, the total number of coincidence events corresponding to the LOR, or the like, or any combination thereof. The imaging data may further include TOF information of a plurality of coincidence events. The TOF information of a coincidence event may include a time difference (e.g., a TOF difference) between two detection times of two gamma photons in the coincidence event, an estimated annihilation location on an LOR where the two gamma photons are generated in the coincidence event (or an estimated annihilation location on an LOR at which a positron-electron annihilation corresponding to the coincidence event takes place), or the like, or any combination thereof. The estimated annihilation location of a coincidence event may include a probability distribution of annihilation location on the LOR at which two gamma photons generated in the coincidence event.

In 620, the first back projection module 520 may generate, based on a back projection algorithm, a first back projection image by reconstructing the imaging data including time of flight (TOF) information. The first back projection image may be a two-dimensional (2D) image or a three-dimensional (3D) image. For a coincidence event, an estimated annihilation location (e.g., a probability distribution of the annihilation location) on an LOR may be determined based on the TOF information of the coincidence event (e.g., the time difference). Similarly, one or more estimated annihilation locations (e.g., one or more probability distribution of the annihilation location(s)) on the LOR corresponding to one or more coincidence events may be determined based on the TOF information of the coincidence event(s). The first back projection module 520 may determine the first back projection image by reconstructing the imaging data including the estimated annihilation location(s) (e.g., the probability distribution(s) of the annihilation location(s)) on the LOR corresponding to the coincidence event(s) using the back projection algorithm. In some embodiments, the generated first back projection image may include a plurality of voxels or pixels.

In some embodiments, the back projection algorithm may relate to a plurality of projections associated with at least one coincidence event onto a plurality of projection planes (e.g., detector units) at different projection angles. A projection angle refers to an included angle between an LOR and a horizontal line. In some embodiments, the first back projection module 520 may generate the first back projection image using the back projection algorithm based on the projections at all projection angles of 360° of the at least one coincidence event. In some embodiments, the first back projection module 520 may generate the first back projection image using the back projection algorithm based on the projections at one or more of the all projection angles of 360° (e.g., 0°, 60°, 120°, 180°, 240°, 300°, etc., or a combination thereof) of the at least one coincidence event.

In some embodiments, the first back projection module 520 may perform a correction operation to the imaging data. The correction operation may include a normalized correction, an attenuation correction, a system dead time correction, or the like, or any combination thereof. In some embodiments, the first back projection module 520 does not perform any correction operation.

In 630, the second back projection module 530 may generate, based on a back projection algorithm, a second back projection image by reconstructing the imaging data excluding the TOF information. In some embodiments, the back projection algorithm used by the second back projection module 530 may be the same as the back projection algorithm used by the first back projection module 520. The second back projection image may be a 2D image or a 3D image. For a coincidence event, the probabilities of the annihilation location on an LOR may be set same on the LOR if the TOF information is not considered. That is, the probability distribution of the annihilation location on the LOR may be same. The second back projection module 530 may determine the second back projection image by reconstructing the imaging data with same probability distributions on the LOR using the back projection algorithm. In some embodiments, the generated second back projection image may include a plurality of voxels or pixels. The plurality of voxels (or pixels) in the first back projection image may spatially correspond to the plurality of voxels (or pixels) in the second back projection image. A voxel (or pixel) in the first back projection image and a corresponding voxel (or pixel) in the second back projection image relates to a same location in the object.

In some embodiments, the second back projection module 530 may generate the second back projection image using the back projection algorithm based on the projections at all projection angles of 360° of the at least one coincidence event. In some embodiments, the second back projection module 530 may generate the second back projection image using the back projection algorithm based on the projections at one or more of the all projection angles of 360° (e.g., 0°, 60°, 120°, 180°, 240°, 300°, etc., or a combination thereof) of the at least one coincidence event.

In some embodiments, the second back projection module 530 may perform a correction operation to the imaging data. The correction operation may include a normalized correction, an attenuation correction, a system dead time correction, or the like, or any combination thereof. In some embodiments, the second back projection module 530 may not perform any correction operation. A correction operation to the first back projection image or to the second back projection image may correct one or more types of artifact. In some embodiments, the correction operation performed to the first back projection image may be the same as the correction operation performed to the second back projection image. For example, if the normalized correction is performed to the first back projection image, the normalized correction may also be performed to the second back projection image. In some embodiments, neither the first back projection image nor the second back projection image generated as described is subject to a correction operation, which may make the process of accessing the TOF performance of the PET scanner efficiency.

In 640, the comparison module 540 may compare the first back projection image with the second back projection image. In some embodiments, because the first back projection image is generated based on the TOF information, and the second back projection image is generated without the TOF information, ratios of the voxel values (or the pixel values) of the first back projection image to the voxel values (or the pixel values) of the second back projection image may reflect the TOF performance of the PET scanner 110. In some embodiments, because the radiation distributes symmetrically in the object (e.g., a phantom), the better the TOF performance of the PET scanner 110 is, the higher the degree of symmetry of the ratios may be. Therefore, the comparison module 540 may determine a degree of symmetry of the ratios to assess the TOF performance of the PET scanner 110.

In some embodiments, the comparison module 540 may determine one or more ratio images based on the first back projection image and the second back projection image. For example, the first back projection image and the second back projection image may be 3D images corresponding to each other (corresponding to a same portion of the object). The first back projection image may include a plurality of first voxels, and the second back projection image may include a plurality of second voxels. The comparison module 540 may determine one or more 2D ratio images in each of which the pixel values of the pixels are ratios of the voxel values of a part of the plurality of first voxels to the voxel values of a corresponding part of the plurality of second voxels. More description in this regard may be found elsewhere in the present disclosure. See, e.g., FIG. 7 and FIG. 8 and the description thereof. Alternatively, the comparison module 540 may determine one or more 3D ratio images in each of which the voxel values of the voxels are ratios of the voxel values of the first voxels to the voxel values of the second voxels. As another example, the first back projection image and the second back projection image may be 2D images corresponding to each other (corresponding to a same portion of the object). The comparison module 540 may determine a 2D ratio image in which the pixel values of the pixels are ratios of the pixel values of pixels in the first back projection image to the pixel values of pixels in the second back projection image.

For each of the one or more 2D ratio images (or 3D ratio images), the comparison module 540 may determine one or more degrees of symmetry of pixel values (or voxel values) in the 2D ratio image (or 3D ratio image). See, e.g., FIG. 9 and FIGS. 12A-12B and the description thereof. For example, the comparison module 540 may determine one or more degrees of symmetry with respect to one or more centers of symmetry and/or one or more degrees of symmetry with respect to one or more axes of symmetry. In some embodiments, the comparison module 540 may determine the one or more degrees of symmetry based on the distribution of the radiation originating from the object. For example, if the object is central symmetric, the radiation originating from the object may demonstrate a central symmetric distribution (e.g., the distribution of the radiation in the object is symmetric about a point), and thus, the comparison module 540 may determine a degree of symmetry of the pixel values (or voxel values) with respect to a center of symmetry. As another example, if the object is axial symmetric, the radiation originating from the object may demonstrate an axial symmetric distribution (e.g., the distribution of the radiation in the object is symmetric about a straight line), and thus, the comparison module 540 may determine a degree of symmetry of pixel values (or voxel values) with respect to an axis of symmetry. As still another example, if the object is central and axial symmetric, the radiation originating from the object may demonstrate a distribution that is central symmetric and axial symmetric, and thus, the comparison module 540 may determine a degree of symmetry of pixel values (or voxel values) with respect to a center of symmetry and/or a degree of symmetry of pixel values (or voxel values) with respect to an axis of symmetry.

For each degree of symmetry, the comparison module 540 may determine whether the degree of symmetry is acceptable. The comparison module 540 may compare the degree of symmetry with a threshold. The comparison module 540 may deem the degree of symmetry acceptable in response to the determination that the degree of symmetry is greater than or equal to the threshold. The comparison module 540 may deem the degree of symmetry unacceptable in response to the determination that the degree of symmetry is lower than the threshold. In some embodiments, the comparison module 540 may deem the degree of symmetry unacceptable in response to the determination that the degree of symmetry is equal to the threshold.

In 650, the TOF performance assessment module 550 may assess, based on the comparison, the TOF performance of the PET scanner. In some embodiments, the TOF performance assessment module 550 may assess the TOF performance based on the one or more degrees of symmetry. In some embodiments, the comparison module 540 may determine whether there is at least one of the one or more degrees of symmetry that is unacceptable. The comparison module 540 may deem the TOF performance of the PET scanner 110 acceptable in response to the determination that all of the one or more degrees of symmetry are deemed acceptable. The comparison module 540 may deem the TOF performance of the PET scanner 110 unacceptable in response to the determination that at least one of the one or more degrees of symmetry is deemed unacceptable.

Figure 7:
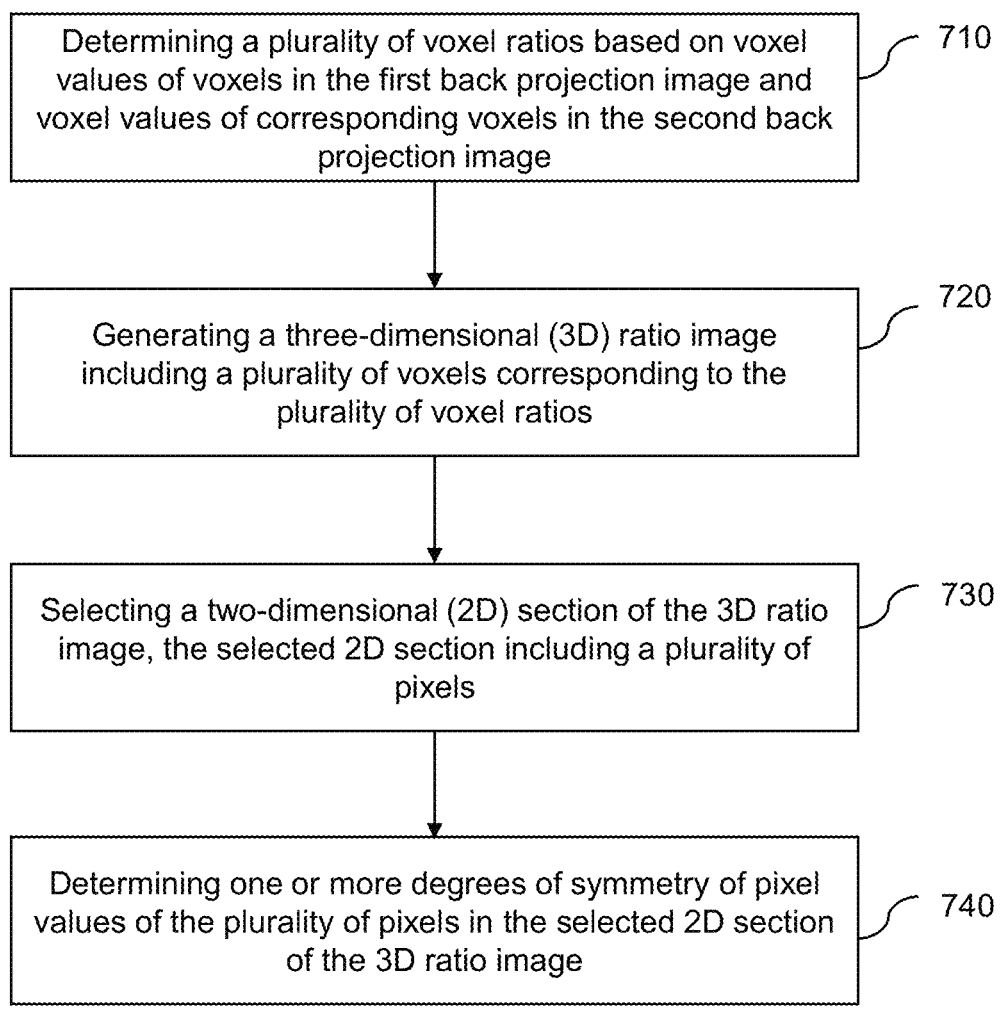
FIG. 7 is a flowchart illustrating an exemplary process for comparing a first back projection image with a second back projection image according to some embodiments of the present disclosure.

FIG. 7 is a flowchart illustrating an exemplary process for comparing a first back projection image with a second back projection image according to some embodiments of the present disclosure. The process 700 may be implemented in the PET system 100 illustrated in FIG. 1. For example, the process 700 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, step 640 illustrated in FIG. 6 may be performed according to the process 700. In some embodiments, the process 700 may be used to determine one 2D ratio image. The comparison module 540 may determine two or more 2D ratio images by repeating the process 700 one by one or simultaneously.

In 710, the comparison module 540 may determine a plurality of voxel ratios based on the voxel values of voxels in the first back projection image and the voxel values of corresponding voxels in the second back projection image. Merely by way of example, the first back projection image and the second back projection image may be 3D images. The voxels in the second back projection image may correspond to the voxels in the first back projection image. In some embodiments, the comparison module 540 may determine the plurality of voxel ratios by dividing the voxel values of the voxels in the first back projection image by the voxel values of the corresponding voxels in the second back projection image, respectively, or by dividing the voxel values of the voxels in the second back projection image by the voxel values of the corresponding voxels in the first back projection image, respectively. A voxel in the first back projection image and a corresponding voxel in the second back projection relate to a same location in the object.

In 720, the comparison module 540 may generate a three-dimensional (3D) ratio image including a plurality of voxels corresponding to the plurality of voxel ratios. The voxels in the 3D ratio image may correspond to the voxels in the first back projection image and/or the voxels in the second back projection image. A voxel value of a voxel in the 3D ratio image may equal a voxel ratio of the voxel value of a voxel in the first back projection image to the voxel value of a corresponding voxel in the second back projection image.

Figure 10A:
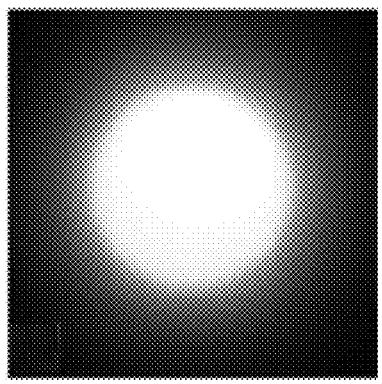
FIG. 10A shows an exemplary 2D section of a first back projection image generated based on TOF information according to some embodiments of the present disclosure.
Figure 10B:
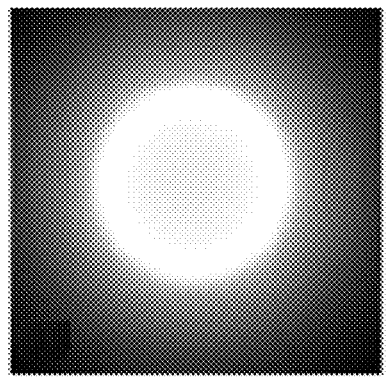
FIG. 10B shows an exemplary 2D section of a second back projection image generated without TOF information according to some embodiments of the present disclosure.
Figure 10C:
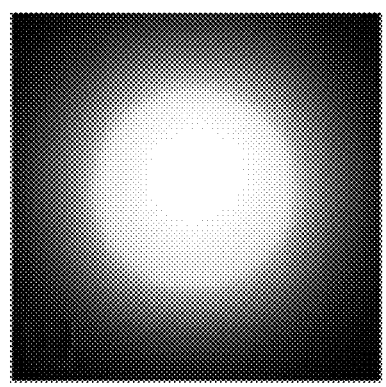
FIG. 10C shows an exemplary 2D ratio image according to some embodiments of the present disclosure.

In 730, the comparison module 540 may select a two-dimensional (2D) section (e.g., also referred to as a 2D ratio image) (e.g., as shown in FIG. 10C) of the 3D ratio image. The selected 2D section of the 3D ratio image may include a plurality of pixels that correspond to a portion of voxels in the 3D ratio image.

A pixel value of a pixel in the selected 2D section may be equal to a voxel value (e.g., a voxel ratio) of a corresponding voxel in the 3D ratio image. In some embodiments, the comparison module 540 may randomly select the 2D section of the 3D ratio image. Alternatively, the comparison module 540 may select a specific 2D section of the 3D ratio image. For example, a series of 2D sections may be selected from the 3D ratio image sequentially along the Z direction as shown in FIG. 2. The comparison module 540 may select a 2D section that is in the middle of the series.

In 740, the comparison module 540 may determine one or more degrees of symmetry of pixel values in the selected 2D section of the 3D ratio image. In some embodiments, the comparison module 540 may determine one or more degrees of symmetry of pixel values in the 2D section with respect to one or more centers of symmetry and/or one or more degrees of symmetry of pixel values in the 2D second with respect to one or more axes of symmetry. If the pixel values in the 2D section are symmetric about a point, the point is referred to as a center of symmetry. If the pixel values in the 2D section are symmetric about a straight line, the straight line is referred to as an axis of symmetry.

Figure 8:
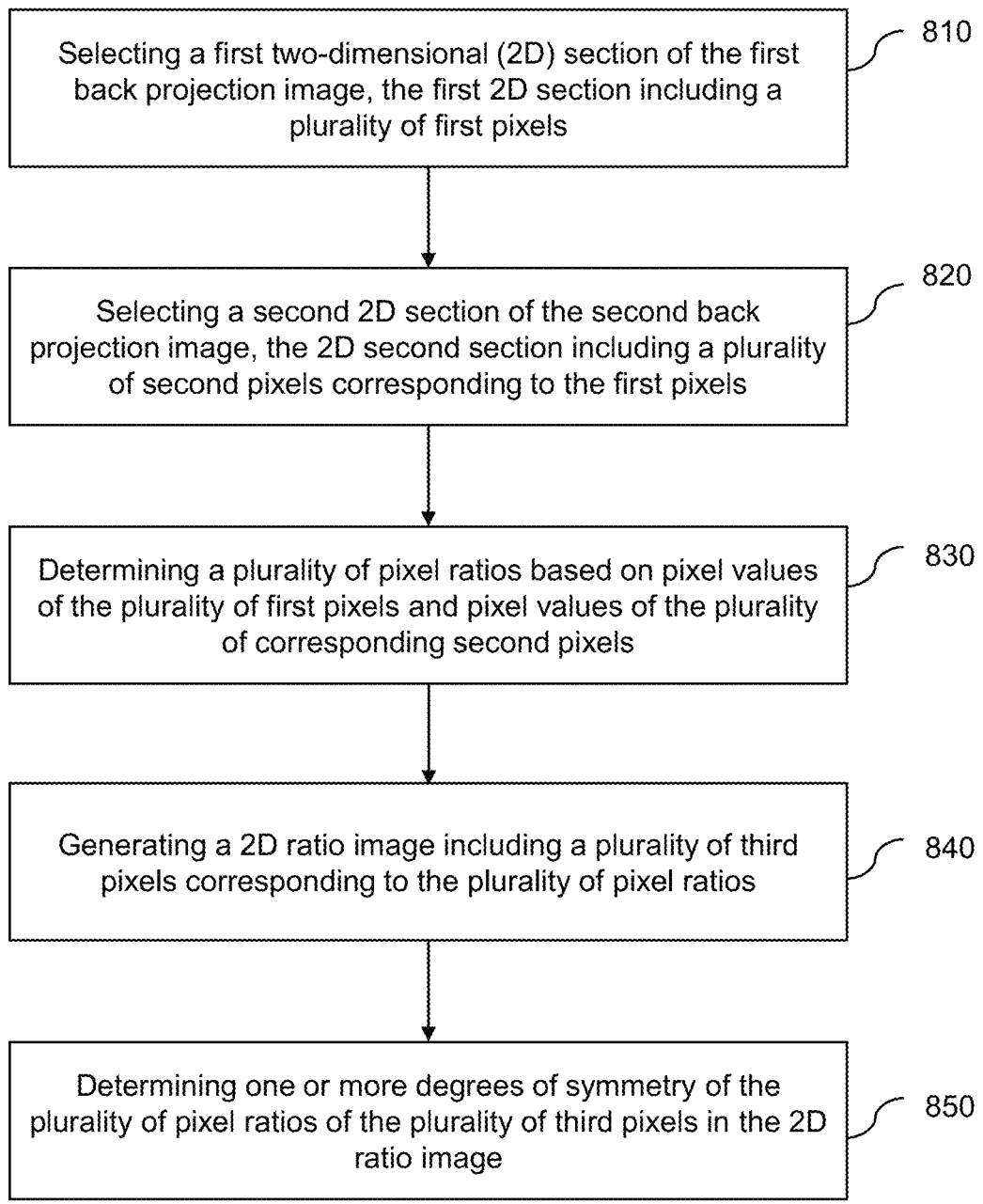
FIG. 8 is a flowchart illustrating an exemplary process for comparing the first back projection image with the second back projection image according to some embodiments of the present disclosure.

FIG. 8 is a flowchart illustrating an exemplary process for comparing the first back projection image with the second back projection image according to some embodiments of the present disclosure. The process 800 may be implemented in the PET system 100 illustrated in FIG. 1. For example, the process 800 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, step 640 illustrated in FIG. 6 may be performed according to process 800. In some embodiments, the process 800 may be used to determine one 2D ratio image. The comparison module 540 may determine two or more 2D ratio images by repeating the process 800 one by one or simultaneously.

In 810, the comparison module 540 may select a first two-dimensional (2D) section (e.g., as shown in FIG. 10A) of the first back projection image. Merely by way of example, the first back projection image may be a 3D image. The first 2D section may include a plurality of first pixels. A first pixel may correspond to a voxel in the first back projection image. A pixel value of a first pixel in the first 2D section may be equal to a voxel value of a corresponding voxel in the first back projection image. In some embodiments, the comparison module 540 may randomly select the first 2D section. Alternatively, the comparison module 540 may select a specific 2D section of the first back projection image as the first 2D image. For example, a series of 2D sections of the first back projection image may be selected from the first back projection image sequentially along the Z direction as shown in FIG. 2. The comparison module 540 may select a 2D section that is in the middle of the series as the first 2D section.

In 820, the comparison module 540 may select a second 2D section (e.g., as shown in FIG. 10B) of the second back projection image. Merely by way of example, the second back projection image may be a 3D image. The second 2D section may include a plurality of second pixels. A second pixel may correspond to a voxel in the second back projection image. A pixel value of a second pixel in the second 2D section may be equal to a voxel value of a corresponding voxel in the second back projection image. In some embodiments, the comparison module 540 may randomly select the second 2D section. Alternatively, the comparison module 540 may select a specific 2D section of the second back projection image as the second 2D image. For example, a series of 2D sections of the second back projection image may be selected from the second back projection image sequentially along the Z direction as shown in FIG. 2. The comparison module 540 may select a 2D section that is in the middle of the series as the second 2D section.

In 830, the comparison module 540 may determine a plurality of pixel ratios based on pixel values of the plurality of first pixels and pixel values of the plurality of corresponding second pixels. In some embodiments, the comparison module 540 may determine the plurality of pixel ratios by dividing the pixel values of the plurality of first pixels by the pixel values of the plurality of corresponding second pixels, respectively, or by dividing the pixel values of the plurality of second pixels by the pixel values of the plurality of corresponding first pixels, respectively. A pixel in a 2D portion of the first back projection image and a corresponding pixel in a 2D portion of the second back projection relates to a same location in the object.

In 840, the comparison module 540 may generate a 2D ratio image (e.g., as shown in FIG. 10C) including a plurality of third pixels corresponding to the plurality of pixel ratios. The plurality of third pixels may spatially correspond to the plurality of first pixels and/or the plurality of second pixels. A third pixel and a corresponding first (or second) pixel relates to a same location in the object. A pixel value of a third pixel may be equal a pixel ratio of the pixel value of a first pixel to the pixel value of a corresponding second pixel.

In 850, the comparison module 540 may determine one or more degrees of symmetry of pixel values in the 2D ratio image. In some embodiments, the comparison module 540 may determine one or more degrees of symmetry of pixel values in the 2D ratio image with respect to one or more centers of symmetry and/or one or more degrees of symmetry of pixel values in the 2D ratio image with respect to one or more axes of symmetry according to the technique similar to that described in connection with 740, which is not repeated here.

Figure 9:
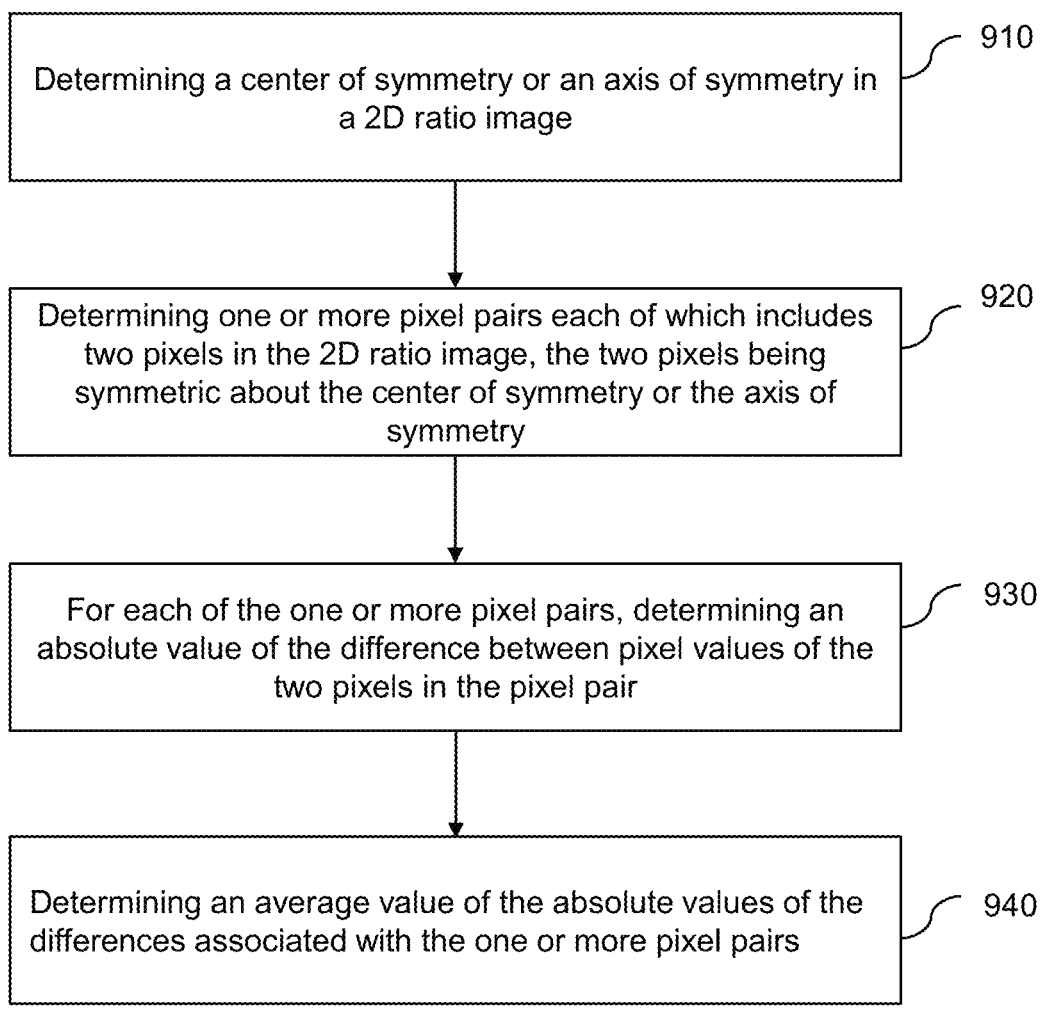
FIG. 9 is a flowchart illustrating an exemplary process for determining a degree of symmetry related to a two-dimensional (2D) ratio image according to some embodiments of the present disclosure.

FIG. 9 is a flowchart illustrating an exemplary process for determining a degree of symmetry related to a 2D ratio image according to some embodiments of the present disclosure. The process 900 may be implemented in the PET system 100 illustrated in FIG. 1. For example, the process 800 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, step 740 illustrated in FIG. 7 and/or step 850 illustrated in FIG. 8 may be performed according to process 900. In some embodiments, the process 900 may be used to determine one degree of symmetry. The comparison module 540 may determine two or more degrees of symmetry by repeating the process 900 one by one or simultaneously.

For brevity, the description of determining a degree of symmetry may take 2D ratio image as an example. It should be noted that the description of determining a degree of symmetry described below are merely some examples or implementations. For persons having ordinary skills in the art, the process 900 for determining a degree of symmetry may be applied to other similar situations, such as a 3D ration image.

Figure 11:
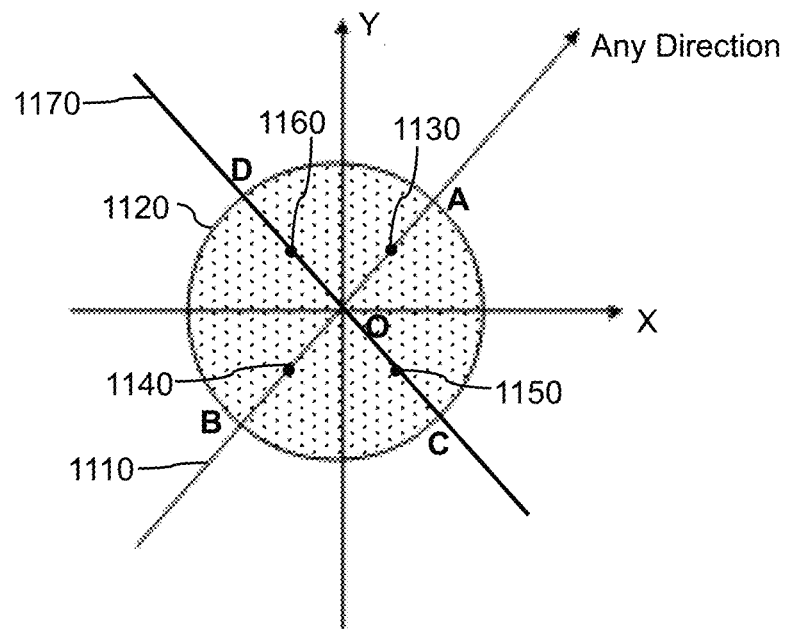
FIG. 11 shows an exemplary 2D ratio image with a circle according to some embodiments of the present disclosure.

In 910, the comparison module 540 may determine a center of symmetry or an axis of symmetry in a 2D ratio image. For example, the radiation in the object distributes within the shape of a column. As shown in FIG. 11, the 2D ratio image may show a cross-section (e.g., a circle 1120) of the column. The comparison module 540 may determine the center of the circle (e.g., a point O in FIG. 11) in the 2D ratio image as the center of symmetry. Alternatively, the comparison module 540 may determine any one of the diameters (e.g., a line 1110 in FIG. 11, a line 1170 in FIG. 11, the X axis in FIG. 11, the Y axis in FIG. 11) of the circle in the 2D image as the axis of symmetry.

In 920, the comparison module 540 may determine one or more pixel pairs each of which includes two pixels in the 2D ratio image. The two pixels may be symmetric with respect to the center of symmetry or the axis of symmetry.

In some embodiments, if the comparison module 540 determines a center of symmetry such as the point O in FIG. 11, the comparison module 540 may determine one or more pixel pairs in each of which the two pixels are symmetric with respect to the center of symmetry. For example, as shown in FIG. 11, a point 1130 and a point 1140 are on the line 1110. The distance between the point 1130 and the point O is equal to the distance between the point 1140 and the point O. The point 1130 and the point 1140 are symmetric with respect to the point O and may be determined as a pixel pair. As another example, as shown in FIG. 11, a point 1150 and a point 1160 are on the line 1170. The distance between the point 1150 and the point O is equal to the distance between the point 1160 and the point O. The point 1150 and the point 1160 are symmetric with respect to the point O and may be determined as a pixel pair.

In some embodiments, if the comparison module 540 determines an axis of symmetry such as the X axis or the Y axis in FIG. 11, the comparison module 540 may determine one or more pixel pairs in each of which the two pixels are symmetric with respect to the axis of symmetry. For example, as shown in FIG. 11, the point 1130 and the point 1150 are on the opposite sides of the X axis, respectively. The distance from the point 1130 to the X axis is equal to the distance from the point 1150 to the X axis. The point 1130 and the point 1150 are symmetric with respect to the X axis and may be determined as a pixel pair. As another example, as shown in FIG. 11, the point 1130 and the point 1160 are on the opposite sides of the Y axis, respectively. The distance from the point 1130 to the Y axis is equal to the distance from the point 1160 to the Y axis. The point 1130 and the point 1160 are symmetric with respect to the X axis and may be determined as a pixel pair.

In 930, for each of the one or more pixel pairs, the comparison module 540 may determine an absolute value of the difference between pixel values (e.g., pixel ratios) of the two pixels in the pixel pair. For example, as shown in FIG. 11, the comparison module 540 may determine an absolute value of the difference between pixel values of the point 1130 and the point 1140. As another example, as shown in FIG. 11, the comparison module 540 may determine an absolute value of the difference between pixel values of the point 1130 and the point 1150. As still another example, as shown in FIG. 11, the comparison module 540 may determine an absolute value of the difference between pixel values of the point 1130 and the point 1160.

In 940, the comparison module 540 may determine an average value of the absolute values of the differences associated with the one or more pixel pairs. In some embodiments, the degree of symmetry of pixel values in the 2D ratio image associated with the symmetric center or the symmetric axis may be represented by the average value. The comparison module 540 may compare the average value with a threshold. The comparison module 540 may deem the degree of symmetry acceptable in response to the determination that the average value is greater than or equal to the threshold. The comparison module 540 may deem the degree of symmetry unacceptable in response to the determination that the average value is lower than the threshold. In some embodiments, the comparison module 540 may deem the degree of symmetry unacceptable in response to the determination that the degree of symmetry is equal to the threshold.

FIG. 10A shows an exemplary 2D section of a first back projection image (e.g., also referred to as a first 2D section) generated based on TOF information. The first 2D section may be selected randomly or regularly. The first 2D section may include a plurality of first pixels. FIG. 10B shows an exemplary 2D section of a second back projection image (e.g., also referred to as a second 2D section) generated without TOF information. The second 2D section may be selected randomly or regularly. The second 2D section may include a plurality of second pixels. FIG. 10C shows an exemplary 2D ratio image according to some embodiments of the present disclosure. The 2D ratio image may include a plurality of third pixels. The plurality of third pixels may spatially correspond to a plurality of first pixels (e.g., the plurality of first pixels in FIG. 10A) and/or the plurality of second pixels (e.g., the plurality of second pixels in FIG. 10B). A third pixel and a corresponding first (or second) pixel relates to a same location in the object. A pixel value of a third pixel may be equal a pixel ratio of the pixel value of a first pixel (e.g., a first pixel in FIG. 10A) to the pixel value of a corresponding second pixel (e.g., a second pixel in FIG. 10B).

Figure 12A:
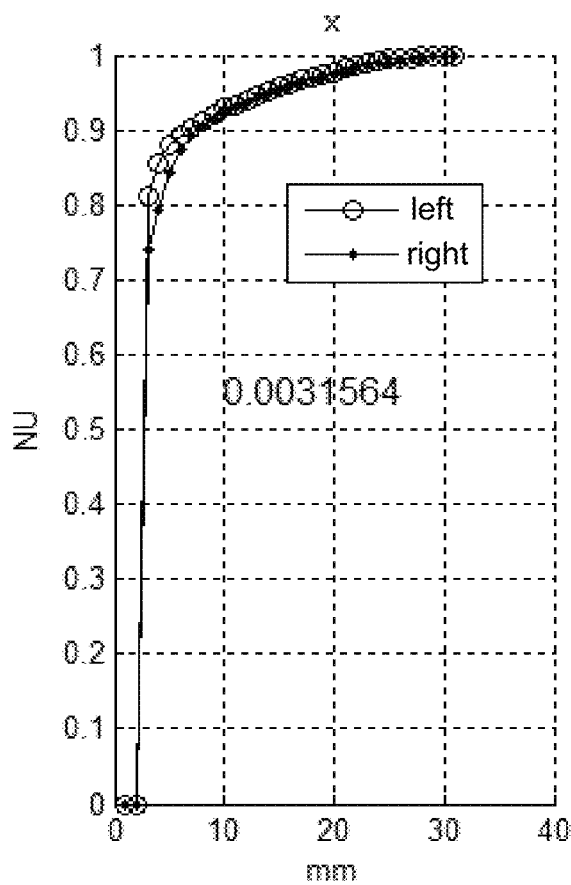
FIGS. 12A and 12B show schematic diagrams illustrating two degrees of symmetry of pixel values in a 2D ratio image according to some embodiments of the present disclosure.

FIG. 12A shows a degree of symmetry of pixel values in a 2D ratio image according to some embodiments of the present disclosure. The degree of symmetry is with respect to the Y axis in FIG. 11. The horizontal axis in FIG. 12A represents a distance (mm) away from the point O in FIG. 11. The vertical axis in FIG. 12A represents a pixel value (NU). A line with a plurality of hollow circles represents pixels (e.g., pixels that are passed through by OB and OD) on the left side of the Y axis in FIG. 11. A line with a plurality of solid circles represents pixels (e.g., pixels that are passed through by OA and OC) on the right side of the Y axis in FIG. 11. OA and OD are symmetric with respect to the Y axis. OC and OB are symmetric with respect to the Y axis. For example, the distance between the point 1130 on OA and the point O is equal to the distance between the point 1160 on OD and the point O. A straight line between the point 1130 and the point 1160 is parallel to the X axis. The point 1130 and the point 1160 may be determined as a pixel pair. As another example, the distance between the point 1140 on OB and the point O is equal to the distance between the point 1150 on OC and the point O. A straight line between the point 1140 and the point 1150 is parallel to the X axis. The point 1140 and the point 1150 may be determined as a pixel pair.

As shown in FIG. 12A, the average value of the absolute values of the differences associated with one or more pixel pairs is 0.0031564. If the threshold is 0.01, the average value indicates that the degree of symmetry of pixel values in the 2D ration image relating to the Y axis is acceptable.

Figure 12B:
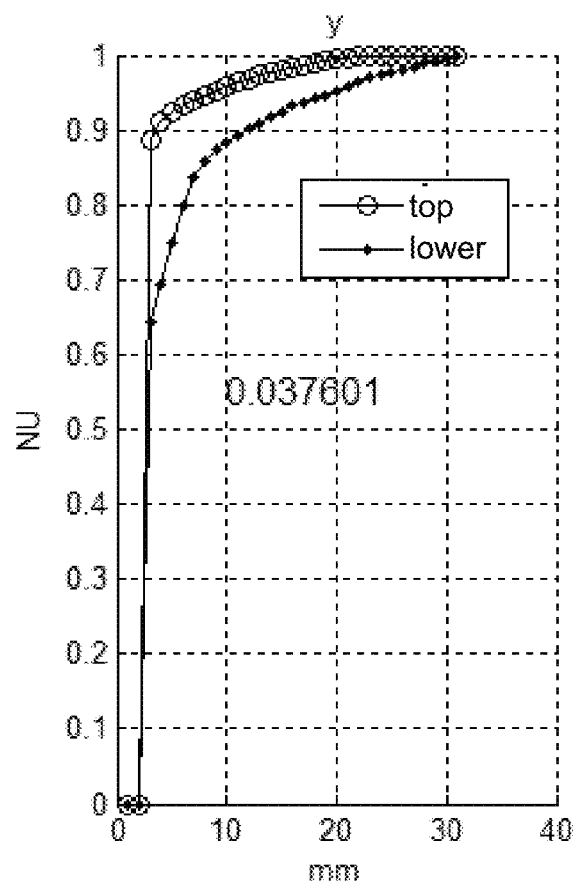

FIG. 12B shows a degree of symmetry of pixel values in the same 2D ratio image as FIG. 12A according to some embodiments of the present disclosure. The degree of symmetry relates to the X axis in FIG. 11. The horizontal axis in FIG. 12B represents a distance (mm) away from the point O in FIG. 11. The vertical axis in FIG. 12B represents a pixel value (NU). A line with a plurality of hollow circles represents pixels (e.g., pixels that are passed through by OA and OD) in the top side of the X axis in FIG. 11. A line with a plurality of solid circles represents pixels (e.g., pixels that are passed through by OB and OC) in the lower side of the X axis in FIG. 11. OA and OC are symmetric about the X axis. OD and OB are symmetric about the X axis. For example, a distance between the point 1130 on OA and the point O is equal to a distance between the point 1150 on OC and the point O. A straight line between the point 1130 and the point 1150 is parallel to the Y axis. The point 1130 and the point 1150 may be determined as a pixel pair. As another example, a distance between the point 1160 on OD and the point O is equal to a distance between the point 1140 on OB and the point O. A straight line between the point 1140 and the point 1160 is parallel to the Y axis. The point 1140 and the point 1160 may be determined as a pixel pair.

As shown in FIG. 12B, the average value of the absolute values of the differences associated with one or more pixel pairs is 0.037601. If the threshold is 0.01, the average value indicates that the degree of symmetry of pixel values in the 2D ration image relating to the X axis is unacceptable.

Because not all of the degrees of symmetry of pixel values in the 2D ratio image are acceptable, the TOF performance assessment module 550 may deem the TOF performance of the PET scanner unacceptable.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system for assessing time of flight (TOF) performance of a positron emission tomography (PET) scanner, comprising:
 at least one storage device storing a set of instructions; and
 at least one processor in communication with the at least one storage device, wherein when the at least one processor executes the set of instructions, the system is caused to effectuate a method including:
  obtaining raw data relating to radiation originating from an object scanned by a PET scanner, the raw data including TOF information, wherein a distribution of the radiation originating from the object is symmetric with respect to a geometrical center of the object;
  generating a first image by reconstructing the raw data including the TOF information;
  generating a second image by reconstructing the raw data excluding the TOF information;
  comparing the first image with the second image; and
  assessing, based on the comparison, a TOF performance of the PET scanner.

2. The system of claim 1, wherein the system is further caused to effectuate the method including:
 performing at least one of a normalized correction, an attenuation correction, or a system dead time correction to the raw data.

3. The system of claim 1, wherein to compare the first image with the second image, the system is caused to effectuate the method including:
 determining a plurality of voxel ratios based on voxel values of voxels in the first image and voxel values of corresponding voxels in the second image;
 generating a three-dimensional (3D) ratio image including a plurality of voxels corresponding to the plurality of voxel ratios; and
 determining one or more degrees of symmetry of the plurality of voxel ratios in the 3D ratio image.

4. The system of claim 3, wherein to assess, based on the comparison, the TOF performance of the PET scanner, the system is caused to effectuate the method including:
 assessing the TOF performance of the PET scanner based on the one or more degrees of symmetry.

5. The system of claim 1, wherein to compare the first image with the second image, the system is caused to effectuate the method including:
 determining a plurality of voxel ratios based on voxel values of voxels in the first image and voxel values of corresponding voxels in the second image;
 generating a three-dimensional (3D) ratio image including a plurality of voxels corresponding to the plurality of voxel ratios;
 determining one or more two-dimensional (2D) ratio images by selecting one or more 2D sections of the 3D ratio image, each of the one or more 2D sections of the 3D ratio image including a plurality of pixels, a pixel value of a pixel in the 2D section being equal to the voxel ratio of a corresponding voxel in the 3D ratio image; and
 for each of the one or more 2D ratio images, determining one or more degrees of symmetry of the pixel values in the 2D ratio image.

6. The system of claim 1, wherein to compare the first image with the second image, the system is caused to effectuate the method including:
 determining one or more 2D ratio images each of which is determined by:
  selecting a first 2D section of the first image, the first section including a plurality of first pixels, a pixel value of a first pixel being equal to a voxel value of a corresponding voxel in the first image;
  selecting a second 2D section of the second image, the second section including a plurality of second pixels, the plurality of second pixels corresponding to the plurality of first pixels, a pixel value of a second pixel being equal to a voxel value of a corresponding voxel in the second image;
  determining a plurality of pixel ratios based on the pixel values of the plurality of first pixels and the pixel values of the plurality of second pixels; and
  generating the 2D ratio image including a plurality of third pixels corresponding to the plurality of pixel ratios; and
 for each of the one or more 2D ratio images, determining one or more degrees of symmetry of the pixel ratios in the 2D ratio image.

7. The system of claim 6, wherein to determine the one or more degrees of symmetry of the pixel ratios in each of the one or more 2D ratio images, the system is caused to effectuate the method including:
 for each of the one or more degrees of symmetry,
  determining a center of symmetry or an axis of symmetry in the 2D ratio image;
  determining one or more pixel pairs each of which includes two pixels in the 2D ratio image, the two pixels being symmetric with respect to the center of symmetry or the axis of symmetry;
  for each of the one or more pixel pairs, determining an absolute value of a difference between pixel values of the two pixels in the pixel pair; and
  determining an average value of the absolute values of the differences associated with the one or more pixel pairs, the average value representing the degree of symmetry.

8. The method of claim 1, wherein the object is located at a center region of a field of view (FOV) of the PET scanner.

9. The system of claim 1, wherein the first image is a first back projection image generated based on a back projection algorithm.

10. The system of claim 1, wherein the second image is a second back projection image generated based on a back projection algorithm.

11. A method for assessing time of flight (TOF) performance of a positron emission tomography (PET) scanner implemented on a computing device having at least one processor and at least one storage medium, the method comprising:
 obtaining raw data relating to radiation originating from an object scanned by a PET scanner, the raw data including TOF information, wherein a distribution of the radiation originating from the object is symmetric with respect to a geometrical center of the object;

generating a first image by reconstructing the raw data including the TOF information;

generating a second image by reconstructing the raw data excluding the TOF information;

comparing the first image with the second image; and assessing, based on the comparison, a TOF performance of the PET scanner.

12. The method of claim 11, wherein the comparing of the first image with the second image comprises:

determining a plurality of voxel ratios based on voxel values of voxels in the first image and voxel values of corresponding voxels in the second image;

generating a three-dimensional (3D) ratio image including a plurality of voxels corresponding to the plurality of voxel ratios; and determining one or more degrees of symmetry of the plurality of voxel ratios in the 3D ratio image.

13. The method of claim 11, wherein the comparing of the first image with the second image comprises:

determining a plurality of voxel ratios based on voxel values of voxels in the first image and voxel values of corresponding voxels in the second image;

generating a three-dimensional (3D) ratio image including a plurality of voxels corresponding to the plurality of voxel ratios;

determining one or more two-dimensional (2D) ratio images by selecting one or more 2D sections of the 3D ratio image, each of the one or more 2D sections of the 3D ratio image including a plurality of pixels, a pixel value of a pixel in the 2D section being equal to the voxel ratio of a corresponding voxel in the 3D ratio image; and for each of the one or more 2D ratio images, determining one or more degrees of symmetry of the pixel values in the 2D ratio image.

14. The method of claim 13, wherein the determining of the one or more degrees of symmetry of the pixel ratios in each of the one or more 2D ratio images comprises:

for each of the one or more degrees of symmetry, determining a center of symmetry or an axis of symmetry in the 2D ratio image;

determining one or more pixel pairs each of which includes two pixels in the 2D ratio image, the two pixels being symmetric with respect to the center of symmetry or the axis of symmetry;

for each of the one or more pixel pairs, determining an absolute value of a difference between pixel values of the two pixels in the pixel pair; and determining an average value of the absolute values of the differences associated with the one or more pixel pairs, the average value representing the degree of symmetry.

15. The method of claim 13, wherein the assessing of the TOF performance of the PET scanner based on the comparison comprises:

assessing the TOF performance of the PET scanner based on the one or more degrees of symmetry.

16. The method of claim 11, wherein the comparing of the first image with the second image comprises:

determining one or more 2D ratio images each of which is determined by:

selecting a first 2D section of the first image, the first section including a plurality of first pixels, a pixel value of a first pixel being equal to a voxel value of a corresponding voxel in the first image;

selecting a second 2D section of the second image, the second section including a plurality of second pixels, the plurality of second pixels corresponding to the plurality of first pixels, a pixel value of a second pixel being equal to a voxel value of a corresponding voxel in the second image;

determining a plurality of pixel ratios based on the pixel values of the plurality of first pixels and the pixel values of the plurality of second pixels; and generating the 2D ratio image including a plurality of third pixels corresponding to the plurality of pixel ratios; and for each of the one or more 2D ratio images, determining one or more degrees of symmetry of the pixel ratios in the 2D ratio image.

17. The method of claim 11, wherein the first image is a first back projection image generated based on a back projection algorithm.

18. The method of claim 17, wherein the generating of the first image by reconstructing the raw data including the TOF information comprises:

generating the first back projection image based on one or more first projection angles of a first range from 0° to 360°.

19. The method of claim 11, wherein the second image is a second back projection image generated based on a back projection algorithm.

20. The method of claim 19, wherein the generating of the second image by reconstructing the raw data including the TOF information comprises:

generating the second back projection image based on one or more second projection angles of a second range from 0° to 360°.

* * * * *